(12) United States Patent
Neustaedter et al.

(10) Patent No.: US 8,840,573 B2
(45) Date of Patent: Sep. 23, 2014

(54) APPARATUSES FOR AND METHOD OF PREVENTING DECUBITUS ULCERS

(75) Inventors: David Neustaedter, Needham, MA (US); Doug Harris, Kalamazoo, MI (US); Ron Lancaster, Hopkinton, MA (US); Martin W. Stryker, Kalamazoo, MI (US); Michael J. Hayes, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 1084 days.

(21) Appl. No.: 12/229,764

(22) Filed: Aug. 27, 2008

(65) Prior Publication Data

US 2009/0069727 A1    Mar. 12, 2009

Related U.S. Application Data

(60) Provisional application No. 60/966,392, filed on Aug. 28, 2007.

(51) Int. Cl.
| | | |
|---|---|---|
| *A61H 1/00* | (2006.01) | |
| *A61N 1/36* | (2006.01) | |
| *A61M 21/00* | (2006.01) | |
| *A61N 1/20* | (2006.01) | |
| *A61N 1/32* | (2006.01) | |
| *A61H 23/02* | (2006.01) | |

(52) U.S. Cl.
CPC .......... *A61N 1/205* (2013.01); *A61H 2201/165* (2013.01); *A61H 2201/5058* (2013.01); *A61N 1/328* (2013.01); *A61H 23/0263* (2013.01); *Y10S 5/94* (2013.01)

USPC ............. 601/15; 601/21; 607/62; 607/112; 607/152; 5/940

(58) Field of Classification Search
CPC ............. A61M 2021/00; A61M 2021/0005; A61M 2021/0055; A61M 2021/0072; A61M 2021/0083; A61H 39/002; A61H 2201/165; A61H 2201/5058; A61N 1/0484; A61N 1/328; A61N 1/3602; A61N 1/36078
USPC .......... 601/1–2, 15, 18–21, 46–50, 54, 59, 76, 601/86, 90, 98; 607/62, 112, 152; 600/587; 5/906, 915, 940; 128/886
See application file for complete search history.

(56) References Cited

U.S. PATENT DOCUMENTS

| | | |
|---|---|---|
| 3,990,440 A | 11/1976 | Gaylord, Jr. |
| 4,837,872 A | 6/1989 | Dimatteo et al. |
| 5,144,284 A * | 9/1992 | Hammett .................. 340/573.1 |

(Continued)

OTHER PUBLICATIONS

International Search Report and Written Opinion in PCT/US08/10140 dated Nov. 20, 2008.

*Primary Examiner* — Kim M Lewis
*Assistant Examiner* — Kari Petrik
(74) *Attorney, Agent, or Firm* — Warner Norcross & Judd LLP

(57) ABSTRACT

An apparatus for the prevention of decubitus ulcers includes an overlay and a plurality of stimulation segments disposed throughout the overlay, wherein the stimulation segments provide stimulation. At least one sensor is disposed within at least one of the plurality of stimulation segments. A controller is electrically connected to the at least one sensor, wherein the controller gathers data from the sensor, processes the data, and transmits instructions to the stimulation segments.

19 Claims, 4 Drawing Sheets

(56) References Cited

U.S. PATENT DOCUMENTS

| | | |
|---|---|---|
| 6,015,394 A | 1/2000 | Young |
| 6,030,351 A * | 2/2000 | Schmidt et al. ............... 600/592 |
| 6,367,106 B1 * | 4/2002 | Gronsman ....................... 5/709 |
| 7,378,975 B1 * | 5/2008 | Smith et al. ................ 340/573.1 |
| 2005/0159685 A1 * | 7/2005 | Klein et al. ..................... 601/49 |
| 2006/0272097 A1 * | 12/2006 | Dionne et al. .................... 5/713 |
| 2006/0276845 A1 | 12/2006 | George et al. |
| 2011/0239370 A1 * | 10/2011 | Turo et al. ......................... 5/600 |

\* cited by examiner

FIG. 5A  FIG. 5B

APPARATUSES FOR AND METHOD OF PREVENTING DECUBITUS ULCERS

CROSS REFERENCE TO RELATED APPLICATIONS

This application claims the benefit of U.S. Patent Application No. 60/966,392, filed Aug. 28, 2007 and is incorporated by reference herein in its entirety.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to apparatuses and methods for preventing decubitus ulcers, and more particularly to apparatuses and methods of preventing decubitus ulcers before they form and/or preventing progression of already forming lesions likely to otherwise develop into decubitus ulcers.

2. Description of the Background of the Invention

It is well known and very common that persons who are confined to a bed or other surface for long periods of time are at risk for developing decubitus ulcers, also known as bedsores, pressure sores, or pressure ulcers. Decubitus ulcers are areas of damaged skin that result from prolonged pressure on those areas of the skin. Pressure on the skin occurs when the skin is pressed between a bone and a hard surface, such as bed, thereby preventing blood from reaching tissues in a person's body. Lack of blood flow to body tissue causes cell death that forms decubitus ulcers. Decubitus ulcers are most commonly found in persons who have impaired neurological function or vascular problems due to age, accident, or disease, and thus are confined to a bed or other area in a resting position and have difficulty changing position. Such confinement and impairment tends to restrain such persons in the same position putting pressure on the same area of skin for prolonged periods of time.

Various apparatuses and methods of treating decubitus ulcers have been developed, including apparatuses and methods of eliminating already formed decubitus ulcers and apparatuses and methods of preventing decubitus ulcers from forming. One method of treating already formed decubitus ulcers includes employing an apparatus that senses a position of a patient at various points in time. Thereafter, the position information is compared to previous position information to determine whether the patient has exhibited sufficient activity. If the patient has not exhibited sufficient activity, an alarm or other indicator is triggered to alert a nurse or other person that the patient must be moved. In another method, electrodes are attached to a patient's skin at two positions. A first electrode is placed on or immediately adjacent the wound and a second electrode is placed on healthy skin near the wound. Current is supplied to the electrodes such that the current runs through the wound and electrical stimulation of the wound occurs. In yet another method, ultrasound and electrical energy are simultaneously delivered to a selected locus of human tissue to preferably stimulate the production of collagen, thereby providing a rejuvenation of skin in an area wherein the ultrasound and electrical energy are applied.

The prevention of decubitus ulcers is preferred to treating the ulcers. It is best when the ulcers never form because infection and other complications may occur as a result of the formation of decubitus ulcers. One method of preventing decubitus ulcers is to turn a patient on a regular basis, such as every hour or two hours. In such a method, a patient lying on a bed may, for example, be periodically moved from one side to an opposite side. Patients confined to a wheelchair, chair, or other surface may also be moved in such a manner. Another method of preventing decubitus ulcers employs an air distribution device. The device includes a top sheet undercoated with a waterproof yet vapor permeable material, wherein the top sheet and undercoating include over 6000 tiny apertures. The apertures are provided to allow air circulation to keep wounds dry and regulate body temperature. The top sheet and undercoating also absorb vapor and moisture produced by the patient's skin. The device further includes a waterproof central sheet and an absorbent lower sheet attached to the top sheet to form a coverlet for disposal between the patient and a surface.

SUMMARY OF THE INVENTION

According to one aspect of the present invention, an apparatus for the prevention of decubitus ulcers includes an overlay and a plurality of stimulation segments disposed throughout the overlay, wherein the stimulation segments provide stimulation. At least one sensor is disposed within at least one of the plurality of stimulation segments. A controller is electrically connected to the at least one sensor, wherein the controller gathers data from the sensor, processes the data, and transmits instructions to the stimulation segments.

According to another aspect of the present invention, an apparatus for the prevention of decubitus ulcers includes an overlay and a plurality of stimulation segments disposed throughout the overlap, wherein the stimulation segments are adapted to vibrate. The apparatus further includes a garment adapted to be worn by a patient, wherein the overlay is integrated within the garment.

According to yet another aspect of the present invention, a method for treating decubitus ulcers includes the steps of placing an overlay onto a surface and monitoring sensors that receive information from stimulation segments disposed within the overlay. The method further includes the step of activating the stimulation segments based upon information received from the sensors to prompt a patient to move from a first position to a second position.

BRIEF DESCRIPTION OF THE DRAWINGS

FIGS. 5A-5C are top isometric views of further embodiments of an apparatus for the prevention and/or treatment of decubitus ulcers;

Throughout the figures, like or corresponding reference numerals have been used for like or corresponding parts.

Other aspects and advantages of the present application will become apparent upon consideration of the following detailed description.

DETAILED DESCRIPTION

Figure 1:
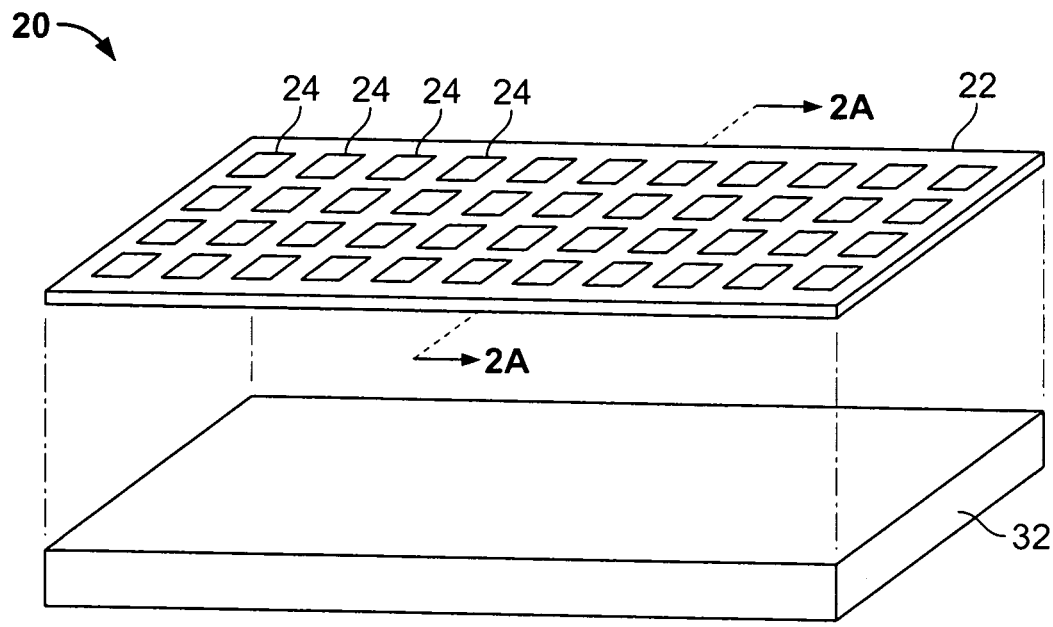
FIG. 1 is a top isometric exploded view of a first embodiment of an apparatus for the prevention and/or treatment of decubitus ulcers.
Figure 2A:
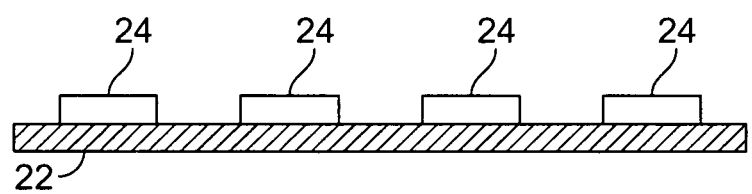
FIG. 2A is a cross-sectional view taken generally along the lines 2A-2A of FIG. 1.
Figure 2B:
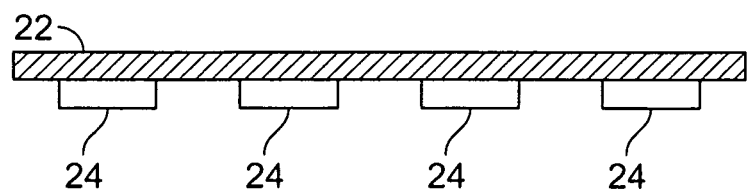
FIGS. 2B and 2C are cross-sectional views similar to that of FIG. 2A depicting alternative arrangements for stimulation segments on an overlay.
Figure 2C:
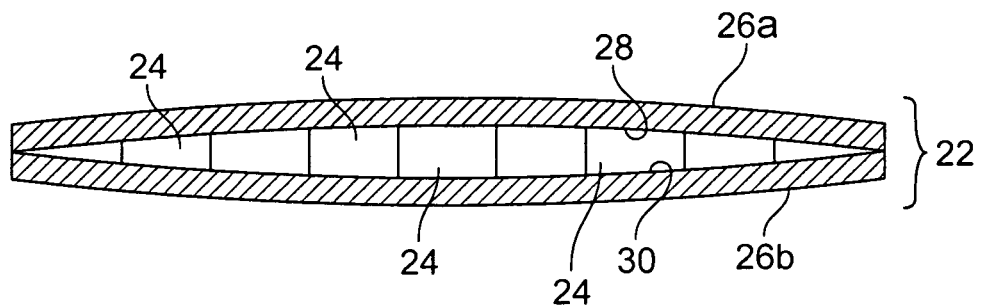
Figure 3:
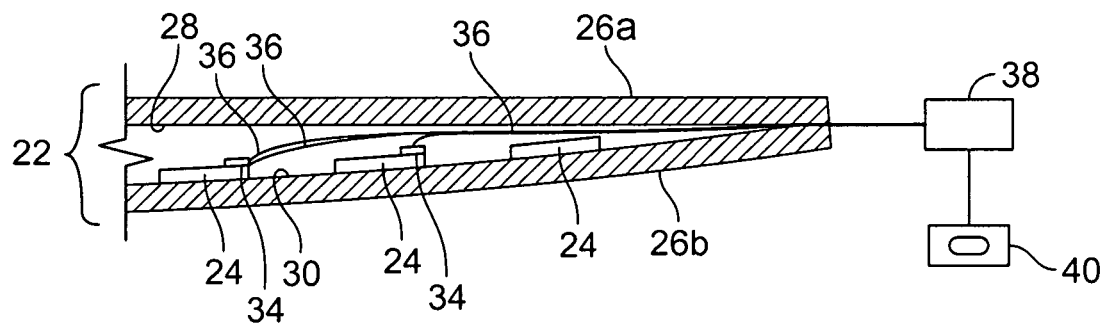
FIG. 3 is an enlarged partial cross-sectional view similar to that of FIG. 2C.

FIGS. 1, 2A-2C, and 3 depict a first embodiment of an apparatus 20 for the prevention and treatment of decubitus ulcers. The apparatus 20 includes an overlay 22 in the form of a blanket, a mat, a pad, a sheet, or other covering. The overlay 22 may be formed of a fabric material, a plastic material, or any other known material for an overlay 22. The overlay 22 includes a plurality of stimulation segments 24 disposed throughout the overlay 22. Although the stimulation segments 24 are shown in FIG. 2A as being disposed atop the overlay 22, the stimulation segments 24 may alternatively be disposed below the overlay 22 as seen in FIG. 2B or between two layers 26a, 26b of the overlay 22 as seen in FIG. 2C. Referring to FIG. 2C, the stimulation segments 24 are shown as sandwiched between the layers 26a, 26b, but may alternatively be attached only to a bottom surface 28 of the layer 26a or an upper surface 30 of the layer 26b (FIG. 3). The stimulation segments 24 may be attached to the overlay 22, the layer 26a, or the layer 26b by an adhesive, hook and loop fasteners, sewing, or any other known method of attachment. Also, although the stimulation segments 24 are shown in a specific pattern, any pattern of stimulation segments 24 is possible.

As seen in FIG. 1, the overlay 22 is disposed atop a surface 32 such as a bed, sofa, chair, wheelchair, or other support surface on which a person would reside. The overlay 22 may simply be placed upon the surface 32 or may be attached to the surface 32 by any attachment means, such as pins, hook and loop fasteners, elastic, adhesive, or the like. One or more of the stimulation segments 24 may include a sensor 34 disposed therein, one of which is shown in FIG. 3. Alternatively, the sensors 34 may be disposed adjacent the stimulation segments 24 or at any area of the overlay 22 where pressure might be applied. The one or more sensors 34 may be strategically placed within stimulation segments 24 so as to be located adjacent points where pressure on the overlay 22 may be greatest or the sensors 34 may be incorporated into all of the stimulation segments 24. The sensors 34 can locate pressure points on a body of a patient and isolate areas of the overlay 22 where the stimulation segments 24 may need to be activated. Activation of the stimulation segments 24 is meant to stimulate or discomfort a patient enough that the patient repositions himself or herself. One or more of the sensors 34 may also measure the intensity and/or duration of the pressure applied by the patient in order to determine the timeframe in which the patient should be repositioned. The one or more sensors 34 may gather information such as patient movement, relative patient location, movement of certain areas of the body but not others, initial and final pressure exertion before first or last pressure on the sensors, etc. Pressure information may be used to determine whether a patient has repositioned oneself and whether the stimulation applied to certain areas of the body is working. The sensors 34 could also measure pulse and/or respiration. This information could be integrated with other patient information and processed according to an algorithm that determines whether and/or where to stimulate the patient.

Referring to FIG. 3, the sensors 34 may be connected by wires 36 to a controller 38. The controller 38 continuously gathers data from the one or more sensors 34, processes the data, and determines when the patient needs to be repositioned based on the data collected. Optionally, the wires 36 may be removed and the sensors 34 may be in wireless communication with the controller 38. Some of such wireless communication devices that may be utilized with any of the embodiments herein are available from Cirronet of Duluth, Ga. or other associated businesses within the Zigbee® Alliance. Wireless communication may provide a more reliable system in damp and/or flexible environments. The controller 38 could include a display 40 for visually depicting the patient and the position of the patient. Any of the embodiments herein may incorporate similar sensors 34 and a controller 38.

Figure 4:
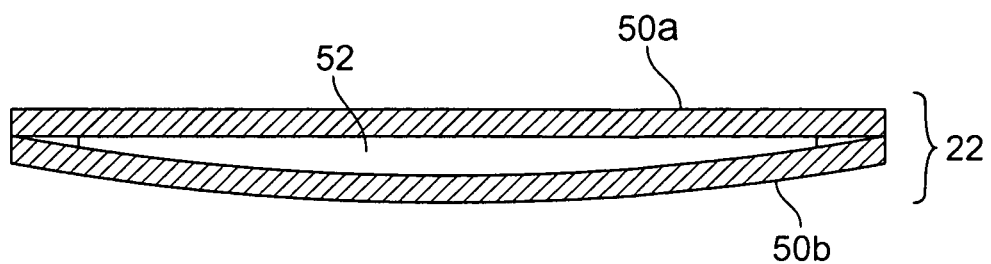
FIG. 4 is a cross-sectional view similar to that of FIG. 2A depicting a further embodiment of an apparatus for prevention and/or treatment of decubitus ulcers.

FIG. 4 depicts a second embodiment of an apparatus similar to that of FIGS. 1, 2A-2C, and 3. In such an embodiment, the entire overlay 22 may be adapted to vibrate or provide electrical current or thermal or acoustic stimulation. For example, the overlay 22 may include first and second layers 50a, 50b of material forming the overlay 22 and a vibrating mat 52 or the like may be disposed between the layers 50a, 50b. The entire vibrating mat 52 is capable of vibrating such that the entirety of the overlay 22 can be vibrated. As with the embodiment of FIG. 3, this embodiment may employ one or more sensors 34 similar to those described in detail above for collecting information with respect to the patient. The sensors 34 may be disposed intermittently throughout one or both of the layers 50a, 50b and or the vibrating mat 52. The overlay 22 of this embodiment may be used for any size or shape of person with a higher degree of accuracy because the entire overlay 22 may be vibrated.

Figure 5C:
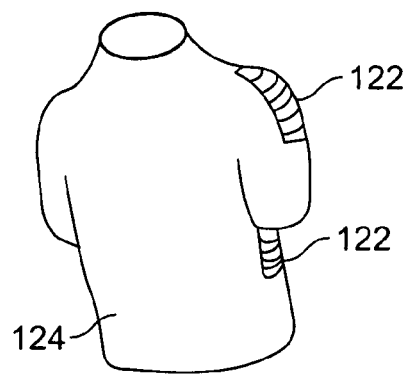
Figure 5C:
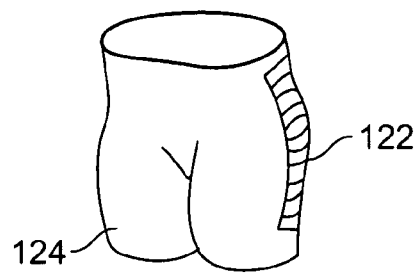
Figure 5C:
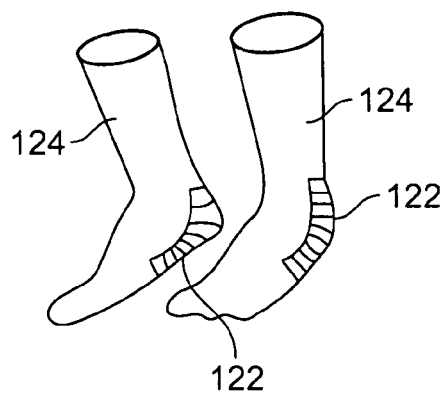
Figure 6:
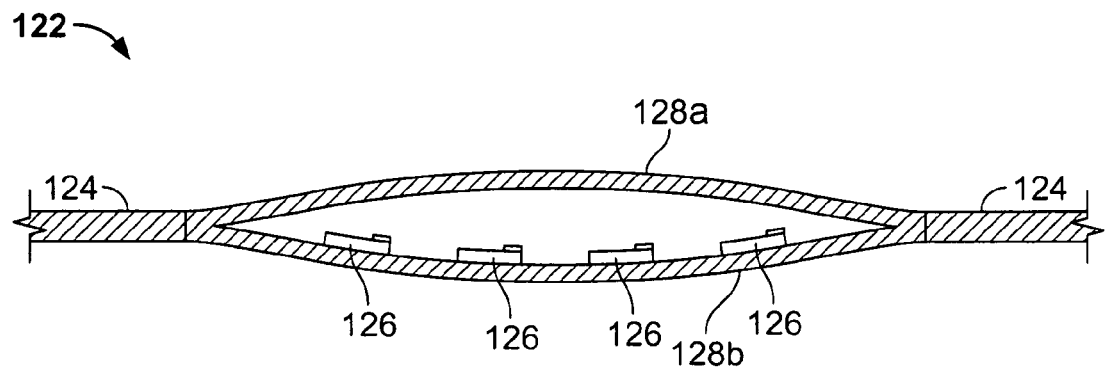
FIG. 6 is a cross-sectional view similar to that of FIG. 2A of a further embodiment of an apparatus for the prevention and/or treatment of decubitus ulcers.

A further embodiment of an apparatus for treating and/or preventing decubitus ulcers is depicted in FIGS. 5A-5C and 6. Referring to FIGS. 5A-5C, an overlay 122 similar to any of the overlays 22 as discussed in detail above with respect to FIGS. 1, 2A-2C, 3, and 4 is incorporated into a garment 124 to be worn by a patient. The garment 124 can be any type of garment 124 worn by a person including, but not limited to, a shirt (FIG. 5A), a pair of shorts or pants (FIG. 5B), or a pair of socks (FIG. 5C). The overlays 122 within the garments 124 may be strategically placed based on common pressure points or personalized pressure points for the particular patient. As seen in FIG. 6, the overlay 122 is seamlessly integrated into the garment 124 such that only a slight difference in thickness may be seen between the garment 124 and the overlay 122. The overlay 122 may be integrated into the garment 124 by any method discussed above with respect to FIGS. 2A-2C. FIG. 6 depicts one implementation of an overlay 122 within a garment 124. The overlay 122 includes a plurality of stimulation segments 126 disposed between fabric layers 128a, 128b that are sewn or otherwise attached to the garment 124. Sensors 134, such as those described above, may be incorporated into the overlay 122, such as within one or more of the stimulation segments 126.

Figure 7:
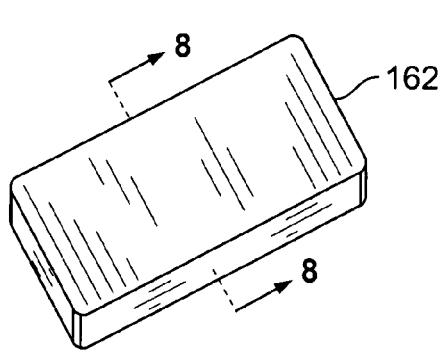
FIG. 7 depicts a mattress for incorporation of a further embodiment of an apparatus for the prevention and/or treatment of decubitus ulcers therein.
Figure 8:
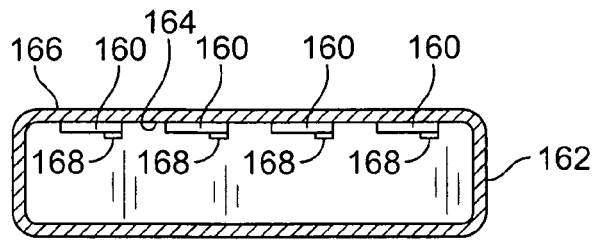
FIG. 8 is a cross-section taken generally along the lines 8-8 of FIG. 7.

FIGS. 7 and 8 depicts another embodiment of an apparatus for preventing initiation and/or progression of decubitus ulcers or skin lesions that could otherwise develop into decubitus ulcers. A plurality of stimulation segments 160 may be incorporated directly into a mattress 162 or other surface such as a chair or a wheelchair seat. For example, the stimulation segments 160 may be attached to a lower side 164 of a top surface 166 of the mattress 162. Sensors 168 may also be utilized as with any of the previous embodiments.

The stimulation segments 24, 124, 160 as disclosed herein are discrete or continuous elements that provide stimulation to a portion of a patient's body upon occurrence of a particular condition or event. The stimulation segments 24, 124, 160 may function through vibration, heat, cooling, chemicals, electrical signals, acoustic signals, or shockwave signals to stimulate and/or alert the patient to move to another position. If the stimulation segments 24, 124, 160 provide electrical signals, each of the segments may include an electrode or an array of electrodes. As discussed above, the electrodes may be distributed through the entire overlay or may be localized to areas of concern, such as the buttocks, side, or heels.

Figure 9:
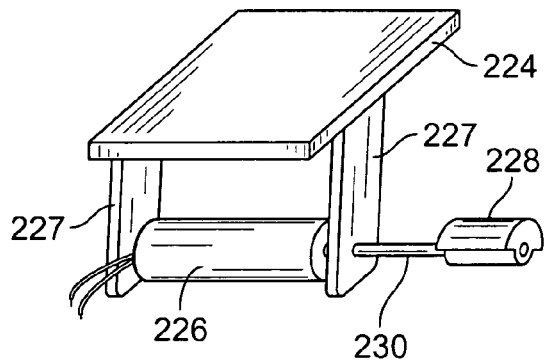
FIGS. 9 and 10 are top isometric views of devices for imparting vibrational energy to one or more stimulation segments.
Figure 10:
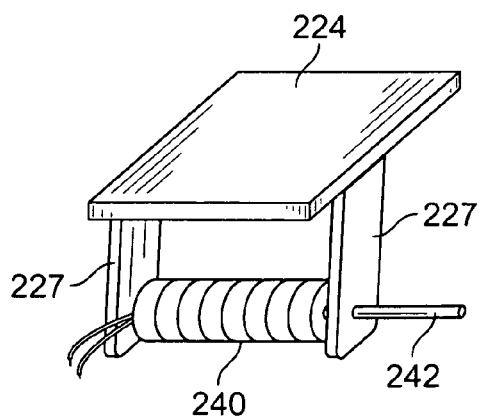

FIGS. 9 and 10 depict devices for providing vibrational energy to the stimulation segments 24, 124, 160. Referring to FIGS. 9 and 10, a single stimulation segment 224 is shown connected to devices for vibrating same, wherein each stimulation segment 224 in a particular overlay would include a similar device to impart vibrational energy thereto. In FIG. 9, a miniature electric motor 226 is connected via arms 227 or the like to the stimulation segment 224. An eccentric weight 228 is connected via a shaft 230 to the motor 226. When the motor 226 spins the weight 228 at a high speed such as between about 100 and about 150 rotations per minute, the asymmetric nature of the weight 228 causes a strong vibration, thus causing the stimulation segment 224 to vibrate. In an alternative arrangement, a gear is connected to the motor such that the motor causes the gear to rotate. A weight is mounted off-center on the gear such that rotation of the gear with the off-center weight thereon causes a strong vibration.

Referring to FIG. 10, a solenoid-type electric apparatus 240 is connected to the stimulation segment 224 by arms 227 or the like. A shaft 242 extending from the solenoid-type apparatus 240 mounts the apparatus 240 to the stimulation segment 224. Quickly turning the electricity provided to a wire coil of the apparatus 240 on and off creates an electromagnetic field that causes the shaft 242 to oscillate, thereby causing vibrations in the stimulation segment 224.

Although a single vibrational element is shown as vibrating a single stimulation segment in FIGS. 9 and 10, any number of vibrational elements may be utilized for a single stimulation segment or a single vibrational element may be utilized to vibrate multiple stimulation segments.

FIGS. 9 and 10 depict just two devices that could be used for vibrating stimulation segments, while any known device or method for vibrating a small member may be utilized.

In a method of preventing decubitus ulcers, an overlay is placed onto a surface where a patient will reside if there is an increased chance that the patient will not be moving much or will be in one position for a long period of time. Sensors in the overlay monitor the patient's position and determine when the patient needs to be repositioned. When it is determined that the patient needs to be repositioned, one or more stimulation segments are activated to cause the patient to move themselves. Alternatively, one or more stimulation segments may be preprogrammed to be activated at intervals to ensure the patient moves at regular intervals. Any of the stimulation segments as disclosed herein may be utilized in such a method. In an alternative but similar method, the overlay is instead incorporated into a garment that the patient will wear.

In a method of treating or eliminating decubitus ulcers, an overlay is placed onto a surface where a patient has been residing and has developed decubitus ulcers. Thereafter, sensors in the overlay monitor the patient's position and determine when the patient needs to be repositioned. When the patient needs to be repositioned, one or more stimulation segments are activated to cause the patient to move themselves. Alternatively, one or more stimulation segments may be preprogrammed to be activated at intervals to ensure the patient moves at regular intervals or that the ulcers are stimulated at regular intervals. The stimulation might be applied specifically to the area of the patient's skin that is of concern, or more broadly, at another location that is targeted by the device but likely to cause the patient to re-position themselves. Any of the stimulation segments as disclosed herein may be utilized in such a method. In an alternative but similar method, the overlay is instead incorporated into a garment that the patient will wear.

INDUSTRIAL APPLICABILITY

The apparatuses and methods as described in detail herein may be used before or after decubitus ulcers have formed. In addition, although the apparatuses and methods disclosed herein are described as being appropriate for the prevention and/or treatment of decubitus ulcers, such apparatuses and methods may also be employed for pain relief, healing of skin wounds, or other skin conditions.

Numerous modifications to the present application will be apparent to those skilled in the art in view of the foregoing description. Accordingly, this description is to be construed as illustrative only and is presented for the purpose of enabling those skilled in the art to make and use the embodiments of the present application and to teach the best mode of carrying out same.

We claim:

1. An apparatus for the prevention of decubitus ulcers in a patient contacting the apparatus, said apparatus comprising: an overlay for placing on a patient support surface; a plurality of stimulation segments disposed at the overlay, said stimulation segments comprising discrete elements each configured to apply electrical energy to a patient's body of sufficient magnitude to cause the patient to reposition themselves; at least one sensor in the overlay for monitoring information about the patient; and a controller in communication with the at least one sensor, and the controller actuating at least one of the stimulation segments upon the occurrence of a condition or event associated with the patient based on the information monitored by the sensor.

2. The apparatus of claim 1, wherein the overlay comprises a blanket, a mat, a pad, a sheet, or other covering.

3. The apparatus of claim 1, wherein the overlay is formed of a fabric material, a plastic material, or combinations thereof.

4. The apparatus of claim 1, wherein the overlay includes at least two layers of material and the stimulation segments are disposed between two layers of the overlay.

5. The apparatus of claim 1, wherein the overlay is adapted to be disposed atop a bed, a mattress, a sofa, a chair, a wheelchair, or other support surface.

6. The apparatus of claim 1, wherein said sensor comprises a plurality of sensors associated with at least some of the stimulation segments and the controller is electrically connect to the plurality of sensors, wherein the sensors are disposed adjacent points where pressure on the overlay may be the greatest.

7. The apparatus of claim 6, wherein the instructions comprise activation of the stimulation segments in a specific pattern corresponding to points on a patient's body.

8. The apparatus of claim 6, wherein the controller continuously gathers data from one or more of the sensors, processes the data, and determines when a patient needs to be repositioned based on the data collected.

9. The apparatus of claim 8, wherein the controller is wirelessly connected to the sensors.

10. The apparatus of claim 1, wherein in addition to the electrical energy, the overlay provides thermal stimulation or acoustic stimulation or mechanical stimulation.

11. The apparatus of claim 1, wherein said support apparatus includes a plurality of said sensors, each sensor monitoring information about the patient and being associated with a respective stimulation segment, and said controller actuating a respective stimulation segment in response to its associated sensor wherein said controller targets specific locations of the patient's body to be stimulated based on information about the patient.

12. A patient support apparatus for supporting a patient, said apparatus comprising:
   a patient support surface;
   an overlay on said patient support surface;
   a plurality of stimulation segments disposed at the overlay, said stimulation segments comprising discrete elements each configured to provide electrical energy to a portion of the patient's body to cause the patient to reposition themselves;
   at least one sensor in the overlay for monitoring information about the patient; and
   a controller in communication with the at least one sensor, and the controller actuating at least one of the stimulation segments upon the occurrence of a condition or event associated with the patient based on the information monitored by the sensor.

13. The apparatus of claim 12, wherein the stimulation segments further generate a stimulation selected from the group consisting of vibration, heat, cool, acoustical signals, and shock waves.

14. The apparatus of claim 12, wherein the plurality of stimulation segments are located throughout the overlay.

15. The apparatus of claim 12, wherein the plurality of stimulation segments are localized in a region selected from the group of a buttock region and a heel region of the overlay.

16. The apparatus of claim 12, wherein the controller gathers information data from the sensor, processes the data, and determines when the patient needs to be repositioned based on the collected data.

17. The apparatus of claim 16, wherein when the controller determines that the patient needs to be repositioned, the controller actuates more than one stimulation segment.

18. The apparatus of claim 12, wherein when the sensor is associated with at least one stimulation segment.

19. The apparatus of claim 12, wherein said support apparatus includes a plurality of said sensors, each sensor monitoring information about the patient and being associated with a respective stimulation segment, and said controller actuating at least one respective stimulation segment in response to its associated sensor wherein said controller targets specific locations of the patient's body to be stimulated based on information about the patient.

* * * * *